United States Patent
Patel et al.

(10) Patent No.: US 10,335,157 B2
(45) Date of Patent: Jul. 2, 2019

(54) ASYMMETRICAL SURGICAL CLIP WITH PENETRATING LOCK, NON-SLIP CLAMPING SURFACE, SEVERABLE HINGE, HINGE BOSS AND PIVOTING APPLICATOR TIP

(75) Inventors: Manoj B. Patel, Irvine, CA (US); David Albala, Manlius, NY (US)

(73) Assignee: Covidien LP, Mansfield, MA (US)

( * ) Notice: Subject to any disclaimer, the term of this patent is extended or adjusted under 35 U.S.C. 154(b) by 337 days.

(21) Appl. No.: 12/896,857

(22) Filed: Oct. 2, 2010

(65) Prior Publication Data

US 2012/0083803 A1    Apr. 5, 2012

(51) Int. Cl.

| A61B 17/00 | (2006.01) |
|---|---|
| A61B 17/29 | (2006.01) |
| A61M 39/28 | (2006.01) |
| A61B 17/122 | (2006.01) |
| A61B 17/128 | (2006.01) |

(52) U.S. Cl.
CPC ........ *A61B 17/122* (2013.01); *A61B 17/1285* (2013.01); *A61B 2017/00858* (2013.01); *A61B 2017/2929* (2013.01); *A61M 39/284* (2013.01)

(58) Field of Classification Search
CPC ....... A61B 17/08; A61B 17/083; A61B 17/12; A61B 17/076; A61B 17/068; A61B 17/122; A61B 17/1227; A61B 17/282; A61B 2017/2825; A61B 17/0487; A61B 17/1285; A61B 17/320092; A61B 2017/12004; A61B 2017/2808; A61B 2017/2926; A61B 2018/0225; A61F 6/20; A61F 6/206; A61F 6/202; A61F 2/20; A61F 2/208; A61L 17/00
USPC ................ 606/151–158, 213, 139, 142, 143; 623/23.72; 128/831, 843
See application file for complete search history.

(56) References Cited

U.S. PATENT DOCUMENTS

| 2,668,538 | A | * | 2/1954 | Baker | A61B 17/12009 294/118 |
|---|---|---|---|---|---|
| 3,978,555 | A | * | 9/1976 | Weisenthal | A44B 11/14 24/543 |
| 4,346,869 | A | * | 8/1982 | MacNeill | 251/10 |
| 4,498,476 | A | * | 2/1985 | Cerwin et al. | 606/158 |
| 4,579,118 | A | * | 4/1986 | Failla | A61B 17/122 606/158 |
| 4,976,722 | A | * | 12/1990 | Failla | 606/157 |
| 5,062,846 | A | * | 11/1991 | Oh | A61B 17/122 606/158 |
| 5,609,599 | A | * | 3/1997 | Levin | A61B 17/083 606/151 |
| 5,713,911 | A | * | 2/1998 | Racenet et al. | 606/157 |

(Continued)

*Primary Examiner* — Katrina M Stransky
*Assistant Examiner* — Lindsey Bachman (57) ABSTRACT

A surgical plastic clip with a hinged pair of opposed arms. A male locking pin on the free end of one arm is configured to penetrate tissue in its path when the male locking pin is urged towards a female aperture on the free end of second arm. A clamping side of one arm includes a wedge-shaped feature, and a clamping side of the second arm includes a V-shaped trough that conforms to the shape of the wedge shaped feature. Each clamping side includes non-slip protrusions such as non-slip protruding ribs. A clip applicator includes a pivoting jaw assembly that pivots at an angle relative to the longitudinal axis of the shaft of the applicator.

17 Claims, 10 Drawing Sheets

(56) References Cited

U.S. PATENT DOCUMENTS

| | | | | |
|---|---|---|---|---|
| 5,921,991 | A * | 7/1999 | Whitehead | A61B 17/122 606/119 |
| 6,015,417 | A * | 1/2000 | Reynolds, Jr. | 606/151 |
| 2006/0217749 | A1* | 9/2006 | Wilson et al. | 606/157 |
| 2009/0275902 | A1* | 11/2009 | Heeps et al. | 604/285 |

* cited by examiner

ASYMMETRICAL SURGICAL CLIP WITH PENETRATING LOCK, NON-SLIP CLAMPING SURFACE, SEVERABLE HINGE, HINGE BOSS AND PIVOTING APPLICATOR TIP

FIELD OF THE INVENTION

The present invention relates to surgical clips, and, more particularly, to a biocompatible surgical clip with a grooved clamping surface to prevent slipping, a severable hinge, a hinge boss to facilitate manipulation and a corresponding applicator with an angularly adjustable tip.

BACKGROUND

A wide number of surgical procedures employ surgical clips (i.e., ligation clips). Such surgical procedures may require vessels, organs or other tissues of the human body to be ligated. Surgical clips ligate, clamp, close off or otherwise occlude the engaged portion of the clamped vessels, organs or other tissues in a surgical site. Such clips may also be used to secure the ends of a suture, as in place of a conventional suture knot.

Ligation can be performed with a ligating clip (i.e., a surgical clip) or by suturing with surgical thread. Suturing requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. So long as the clips and applicator are designed with endoscopic procedures in mind, they are a preferred choice.

The clips are often in the form of thin, narrow, metal or polymeric U-shaped or V-shaped members that are placed over the vessel, tissue or suture material and then forced into a closed position using a clip applicator. Clips constructed of metal, may be initially open and then permanently deformed into a closed or clamped configuration around the desired blood vessel or other tissue structure using an appropriate clip applicator. However, metal clips, which are radio-opaque, interfere with x-ray imaging. Plastic clips include a latch feature to ensure that the clip remains closed with sufficient force to provide full and complete hemostasis or occlusion and to ensure that the clip will not loosen or open over time.

While ligating clips are an improvement over suturing in many procedures, they suffer shortcomings. First the clips typically require a surgical plane or window to be made prior to attachment. Conventional clips are not configured to penetrate tissue. Accurate planning and windowing manipulations are time-consuming and difficult to perform, particularly in endoscopic surgical procedures, which are characterized by limited space and visibility. Furthermore, creating windows can cause extensive bleeding, leading to decreased visibility.

Second, the clips tend to slip as they are applied. Slipping makes accurate placement extremely difficult. To overcome slipping, excessive force may be applied, which can damage the clamped vessel, tissue or organ. Additionally, forces applied during slipping may cause the contact surfaces of the clamping arms to deviate from parallel.

Third, the clips are extremely difficult to remove. Conventional clips include relatively thick hinge and arm sections that abut and occlude a clamped vessel or tissue. The latch is not releasable. Cutting through such a clip without damaging the clamped vessel or tissue is extremely difficult.

Fourth, conventional clip applicators provide a very limited range of positioning and orientation. This limitation makes accurate placement time-consuming and difficult to perform, particularly in endoscopic surgical procedures, which are characterized by limited space and visibility.

The invention is directed to overcoming one or more of the problems and solving one or more of the needs as set forth above.

SUMMARY OF THE INVENTION

To solve one or more of the problems set forth above, in an exemplary implementation of the invention, a surgical clip includes a pair of opposed arms joined at one end by an integrally formed flexible hinge. Each arm has a free end. One arm includes a male locking pin near the free end. The opposite arm includes a female aperture near the free end. The male locking pin is configured to penetrate tissue in the path of the male locking pin when the male locking pin is urged towards the female aperture. The male locking pin includes a tissue penetrating head. The female aperture engages the male locking pin and resists withdrawal of the head when the head of the male locking pin has been urged through the female aperture. The clip may be comprised of a biocompatible metal or plastic or a bioabsorbable plastic. Each of the pair of arms includes a clamping side. The clamping side of one arm includes a wedge-shaped feature. The clamping side of the second arm includes a V-shaped trough that conforms to the shape of the wedge shaped feature. Each clamping side includes non-slip protrusions such as non-slip protruding ribs. The integrally formed flexible hinge has a reduced thickness and protrudes outwardly from the clamping surfaces of the arms. The hinge may be cut to release the clip without cutting the clamped tissue or vessel.

A clip applicator according to principles of the invention includes a pivoting jaw assembly operably coupled to a rotating cuff. An actuator handle assembly is operably coupled to the pivoting jaw assembly. A rotating cuff is operably coupled to the pivoting jaw assembly. A pivoting control is operably coupled to the pivoting jaw assembly. The jaw assembly includes a pair of opposed pivoting jaws configured to receive and compress a surgical clip upon actuation of the actuator handle assembly. The pivoting jaw assembly is rotatable about the longitudinal axis of the shaft of the applicator upon rotation of a cuff and/or pivotable at an angle relative to the longitudinal axis of the shaft of the applicator upon rotation of cuff.

An exemplary surgical clip includes a pair of opposed arms joined at a hinged end by an integrally formed flexible hinge, each arm having a free end, one arm including a male locking pin near the free end and the opposite arm including a female aperture near the free end, said male locking pin including a tissue piercing head, said tissue piercing head being configured to penetrate tissue in the path of the male locking pin when the male locking pin is urged towards the female aperture. The female aperture includes a shape that engages the male locking pin and resists withdrawal of the head when the head of the male locking pin has been urged through the female aperture.

The flexible hinge is a U-shaped segment that extends from the hinged end of each arm of the pair of opposed arms. A shoulder is between the flexible hinge and the hinged end of each arm of the pair of opposed arms. Each shoulder includes a recess at the end of each arm followed by an angled protrusion towards a space between the pair of opposed arms. The hinged ends of the arms of the pair of opposed arms are configured to abut each other when the surgical clip is closed. A clamped object does not contact the flexible hinge when the surgical clip is closed and the hinge may be cut to release the clamp, without contacting the clamped object. An empty space is maintained between the hinged ends of the arms of the pair of opposed arms and the flexible hinge. The flexible hinge has a hinge thickness and width, and each arm of the pair of opposed arms has an average thickness and width, and the width and/or thickness of the flexible hinge is less than the average width of each arm of the pair of opposed arms.

Optionally, the surgical clip may be comprised of a bioabsorbable plastic. Other materials include biocompatible metals, plastics and composites.

Each of the pair of arms includes a clamping side. The clamping side of one arm includes a wedge-shaped feature. The clamping side of the second arm includes a V-shaped trough that conforms to the shape of the wedge shaped feature. Each clamping side includes non-slip protrusions, such as non-slip protruding ribs.

An exemplary clip includes a plurality of bosses, including a hinge boss, for gripping by an applicator and stabilizing during use. As used herein, a boss is a projection or protuberance that can be engaged by an applicator. The hinge boss is a grippable boss (i.e., a protrusion suitable for gripping) at or near the hinge. Gripping the hinge boss during use prevents undesirable angulation (angular disorientation) of the clip during use with an applicator.

In another aspect of the invention, a clip applicator with a pivoting jaw assembly is provided. The clip applicator includes a pivoting jaw assembly operably coupled to a rotating cuff, an actuator handle assembly operably coupled to the pivoting jaw assembly, and a rotating cuff operably coupled to the pivoting jaw assembly. The jaw assembly includes a pair of opposed pivoting jaws configured to receive and compress a surgical clip upon actuation of the actuator handle assembly. The pivoting jaw assembly pivots at an angle relative to the longitudinal axis of the shaft of the applicator upon rotation of cuff. A linkage operably couples the rotating cuff to the pivoting jaw assembly. The linkage may be a rotatable shaft with a threaded distal end (i.e., end adjacent the jaw assembly). The threaded distal end is threadedly engaged by a lever of the jaw assembly. Rotation of the cuff causes rotation of the linkage, which causes movement of the threadedly engaged lever, which causes pivoting of the jaw assembly.

A surgical clip includes a pair of opposed arms joined at one end by an integrally formed flexible hinge. The hinge is configured to be cut in the event removal of the clip is desired. Accordingly, the hinge has a reduced thickness and/or width and is configured to maintain cutting space between the hinge and the clamping surfaces of the opposed arms. Each arm has a free end. One arm includes a male locking pin near the free end. The opposite arm includes a female aperture near the free end. The male locking pin is configured to penetrate tissue in the path of the male locking pin when the male locking pin is urged towards the female aperture. The male locking pin includes a tissue penetrating head. The female aperture engages the male locking pin and resists withdrawal of the head when the head of the male locking pin has been urged through the female aperture. The clip may be comprised of a biocompatible metal or plastic or a bioabsorbable plastic. Each of the pair of arms includes a clamping side. The clamping side of one arm includes a wedge-shaped feature. The clamping side of the second arm includes a V-shaped trough that conforms to the shape of the wedge shaped feature. Each clamping side includes non-slip protrusions such as non-slip protruding ribs. A clip applicator includes a pivoting jaw assembly operably coupled to a rotating cuff. An actuator handle assembly is operably coupled to the pivoting jaw assembly. A rotating cuff is operably coupled to the pivoting jaw assembly. The jaw assembly includes a pair of opposed pivoting jaws configured to receive and compress a surgical clip upon actuation of the actuator handle assembly. The pivoting jaw assembly pivots at an angle relative to the longitudinal axis of the shaft of the applicator upon rotation of cuff.

BRIEF DESCRIPTION OF THE DRAWINGS

The foregoing and other aspects, objects, features and advantages of the invention will become better understood with reference to the following description, appended claims, and accompanying drawings, where:

Those skilled in the art will appreciate that the figures are not intended to be drawn to any particular scale; nor are the figures intended to illustrate every embodiment of the invention. The invention is not limited to the exemplary embodiments depicted in the figures or the configuration, shapes, relative sizes, ornamental aspects or proportions shown in the figures.

DETAILED DESCRIPTION

Ligating clips according to principles of the invention are uniquely characterized by their tissue-penetrating locking mechanism, a configuration of slip-resisting grooves on the clamping surfaces, their geometric configuration and their material composition. Additionally, a corresponding applicator uniquely provides a swiveling and/or pivoting tip to facilitate accurate placement.

Figure 1:
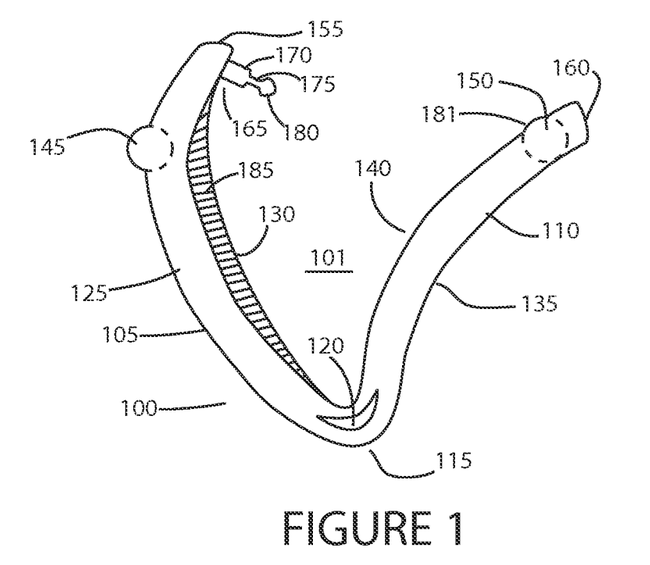
FIG. 1 is a plan view of an exemplary surgical clip according to principles of the invention.
Figures 2, 3:
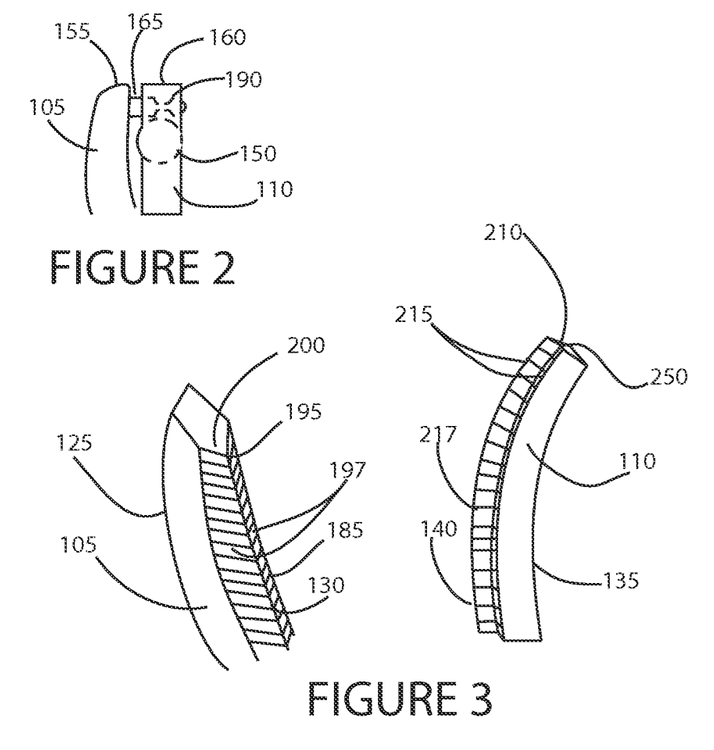
FIG. 2 is a close-up view of an exemplary tip of a surgical clip in a locked configuration according to principles of the invention.
FIG. 3 is first perspective view of exemplary of an exemplary surgical clip according to principles of the invention.

With reference to FIGS. 1 through 3, in one embodiment, a clip 100 according to principles of the invention generally includes a pair of clamping arms 105 and 110, adjoined at an integral flexible hinged joint 115 (the "hinge"), free at the other end 155, 160 and defining an opening 101 therebetween, such as an opening having a generally u- or v-shaped space. The opening 101 is preferably sufficiently wide to engage a vessel, organ or tissue to be ligated. In the exemplary embodiment shown in FIG. 1, the clamping arms 105, 110 are generally rigid. However, the hinged end 115 is sufficiently flexible so that the arms, 105, 110 can be angularly deflected bringing their free ends 155, 160 towards each other to decrease the space between the arms 105, 110, until locking engagement is achieved. In the exemplary clip 100, one or more cutouts 120 formed in the hinge 115 facilitates bending at the hinge 115. Alternatively, other configurations with a reduced cross-sectional area at the hinge 115 may be utilized to facilitate such bending while maintaining structural integrity. Because a clip 100 according to the invention is inserted into a body cavity in a fully opened configuration, the hinge is not required to facilitate expansion.

A first clamping arm 105 extends from the hinge 120. The first clamping arm 105 includes an outer side 125 and a clamping side 130. First arm 105 has a concave clamping side 130 and a convex outer side 125. The clamping side 130 includes protruding V-shaped wedge portion 200. Chamfered (i.e., angled) surfaces 197 converge at a vertex 195. A plurality of protrusions such as protruding teeth or ribs 185 are spaced apart along a portion of the length of the clamping side 130 of clamping arm 105. A boss 145 is provided to facilitate handling and manipulation. A male pin 165 extends from the clamping surface of the first clamping arm 105.

A second clamping arm 110 includes an outer side 135 and a clamping side 140. Second arm 110 has a convex clamping side 140 and a concave outer side 135. The clamping side 140 includes V-shaped trough 210, such as the V-shaped trough conceptually illustrated in FIG. 3. Converging chamfered (i.e., angled) surfaces 215 form the trough 210. The surfaces 215 converge at a vertex (i.e., a point of intersection). Convex clamping side 140 of second arm 110 and concave clamping side of first arm 105 have substantially matching radii of curvature. The trough 210 forms a female receptacle for at least partially receiving the wedge 200 when the arms 105, 110 are urged together. A plurality of protrusions such as protruding teeth or ribs 217 are spaced apart along a portion of the length of the clamping side 140 of clamping arm 110. A boss 150 is provided to facilitate handling and manipulation. A female receptacle 181 is formed in the clamping surface of the second clamping arm 110.

The arrangement and configuration of the wedge and trough may vary within the scope of the invention. For example, the wedge 200 may be formed on the second clamping arm 110 and the trough 210 may be formed on the other arm 105. In this configuration, the wedge 200 may enhance structural integrity of the second arm 110, which may facilitate closure.

Flexible hinge 115 has a continuous concave inner surface and a continuous convex outer surface. Concave inner surface of hinge section 115 joins concave clamping side 130 of first arm 105 and convex clamping side 140 of second arm 110. Convex outer surface of the hinge 115 joins convex outer side 125 of first arm 105 and concave outer side 135 of second arm 110.

An important aspect of an exemplary embodiment is the configuration of non-slip protrusions, such as teeth or ribs. The teeth or ribs are uniquely dimensioned and configured to frictionally engage a vessel, organ or tissue. The teeth or ribs protrude from the clamping-side surface of each clamping arm. The teeth or ribs increase the clamping side pressure and surface area in frictional contact with the engaged vessel, organ or tissue. In the exemplary embodiment, ribs extend radially from the vertices of the chamfered clamping-side surfaces. The height of each rib may preferably be approximately 0.01 to 0.5 mm. A substantially greater height prevents an engaged vessel, organ or tissue from contacting the clamping side surfaces of the clamping arms between ribs, thereby substantially compromising the frictionally engaging surface area. In such a case, the vessel, organ or tissue would be suspended between adjacent ribs. A substantially greater height will also result in a substantially thicker clamp, which can compromise utility in endoscopic procedures.

Figure 4:
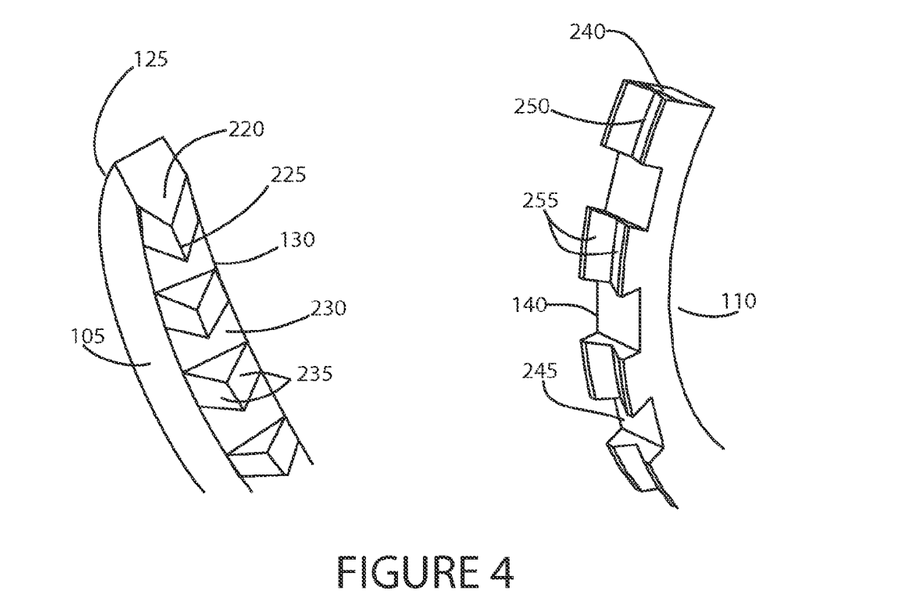
FIG. 4 is a second perspective view of exemplary of an exemplary surgical clip according to principles of the invention.

Referring now to FIG. 4, portions of arms 105, 110 featuring an alternative configuration of clamping surfaces is shown. A plurality of spaced apart wedge shaped protrusions 220 project from the clamping side surface 130 of the first clamping arm 105. Spaces 230 are provided between adjacent wedge-shaped protrusions 220. Each wedge-shaped protrusion 220 is comprised of chamfered (i.e., angled) surfaces 235 that converge at a vertex 225. Correspondingly, spaced apart v-shaped trough segments 240 protrude from the clamping surface 140 of the second clamping arm 110. Spaces 230, 245 are provided between adjacent wedge shaped protrusions 240. Each wedge-shaped protrusion 240 is comprised of chamfered (i.e., angled) surfaces 255 that converge at a vertex 250. The wedges 220 are aligned with the trough segments 240. Thus, when the arms 105, 110 are urged together in locking configuration, the v-shaped troughs 240 receive corresponding wedge shaped protrusions 220. This configuration increases the pressure applied to vessels, organs or tissue sandwiched between the v-shaped troughs 240 and corresponding wedge shaped protrusions 220.

In yet another alternative embodiment, the protrusions are of a size, shape and arrangement so that the protrusions of opposing arms interdigitate with one another when the opposing arms are moved toward one another. By interdigitate it is meant that the protrusions of one arm extend into spaces between counterpart protrusions of the other arm when the arms are moved towards one another. Once the arms are brought together, vessels, organ or other tissue engaged between the arms will be forced under clamping pressure to wind around the protrusions and into the interdigital spaces. The displacement into the interdigital spaces increases the traction and gripping force of the arms upon the engaged vessel, organ or tissue and increases the force required to move the gripped vessel, organ or tissue relative to the arms. In addition, protrusions having gripping features (e.g., ribs) provide additional traction and further resist movement of the gripped vessel, organ or tissue in directions transverse to the gripping edges.

Figure 5:
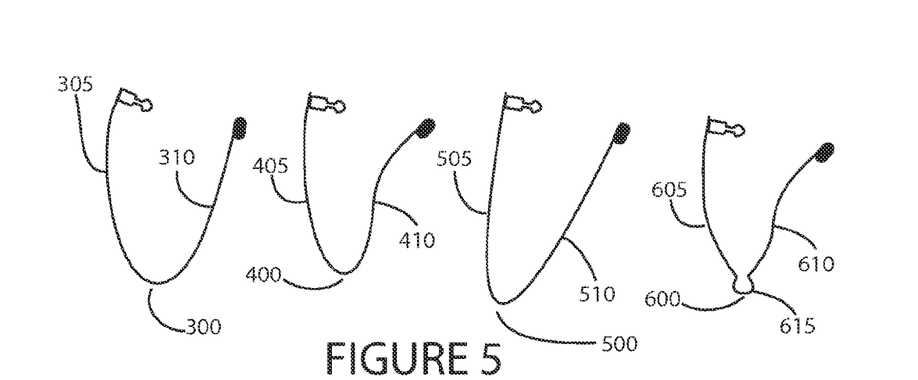
FIG. 5 provides schematics conceptually illustrating various exemplary surgical clip configurations according to principles of the invention.

The shapes of the arms may vary from straight to concave or convex. Referring now to FIG. 5, a configuration 300 with a substantially straight arm 310 and a corresponding curved (i.e., convex) arm 305 is shown. Another embodiment 400 with a pair of curved (i.e., convex) arms 405, 410 is shown. In yet another embodiment 500 a configuration with a pair of substantially straight arms 505, 510 is shown. Another embodiment 600 includes a pair of curved (i.e., convex) arms 605, 610, and a severable hinge 615. In that embodiment, the hinge 615 extends from the converging ends of the arms 605, 610. These and other arm configurations that allow clamping of vessels, organs or tissue between the arms are feasible and come within the spirit and scope of the invention. Thus, two concave surfaces may define a lens shaped space therebetween. A concave and convex surface may define a lune shaped space therebetween. Crescent, circular segment and triangular shapes may also be defined using various combinations of curved and straight arms.

Figure 6:
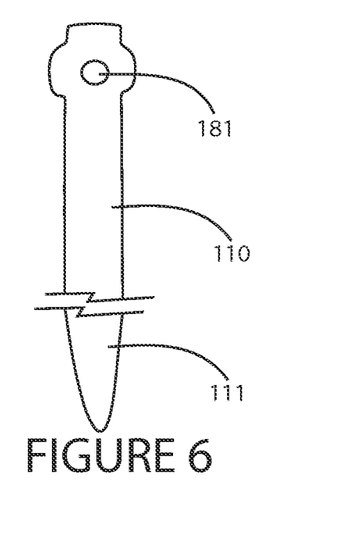
FIG. 6 is a bottom view of an exemplary female receptacle of a locking mechanism for an exemplary surgical clip according to principles of the invention.
Figures 7, 8, 9:
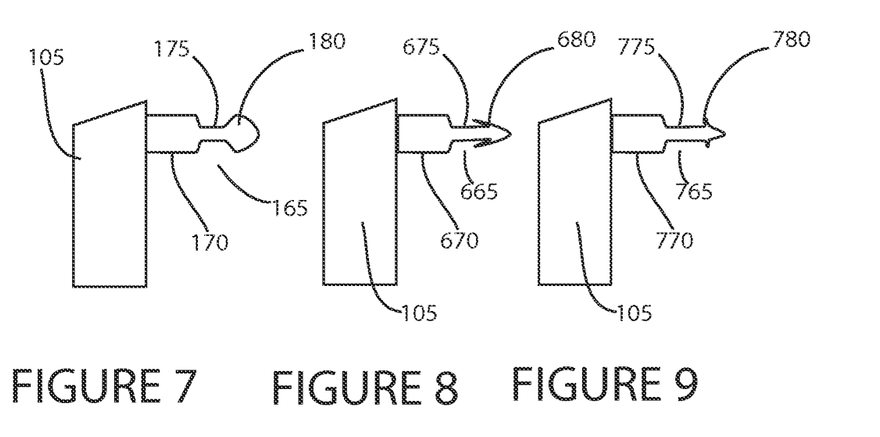
FIG. 7 is a side view of an exemplary male pin of a locking mechanism for an exemplary surgical clip according to principles of the invention.
FIG. 8 is a side view of an exemplary male pin of a locking mechanism for an exemplary surgical clip according to principles of the invention.
FIG. 9 is a side view of an exemplary male pin of a locking mechanism for an exemplary surgical clip according to principles of the invention.

A clip according to principles of the invention includes a male and female locking mechanism, wherein the male component is any of a variety of pins 165, 665, 765 configured to penetrate an engaged tissue or organ. As shown in FIGS. 2 and 6, the female receptacle 181 comprises a resilient aperture in the second arm 110, aligned with the male pin 165. A tapered section 190, flexible tab or other snap fit feature in the receptacle 181 resists withdrawal of the fully inserted male pin 165. As shown in FIGS. 7 through 9, the male pin 165, 665, 765 includes a base 170, 670, 770 which extends from the first arm 105, a shank 175, 675, 775 that extends from the base 170, 670, 770 and a head 180, 680, 780 that extends from the shank 175, 675, 775.

As shown in FIGS. 7 through 9, the head 180, 680, 780 includes a sharpened and/or pointed leading edge suitable for penetrating an engaged portion of an organ or tissue. The head may be rigid biocompatible plastic, reinforced biocompatible plastic, or biocompatible metal.

The head 180, 680, 780 is configured to pass through the opening in the female receptacle 181, yet resist withdrawal. The head 180, 680, 780, the female receptacle 181 or both may exhibit resiliency to allow passage of the head for locking. The bulbous portion, arrow-shape, flanged edge, detents or fingers of the head resist or prevent withdrawal of the head after it has been urged through the female aperture.

Adjacent to the distal (free) ends of the first and second arms and adjacent to the male pin 165 and female aperture 181, a pair of cylindrical bosses 145, 150 are formed coaxially on the opposed lateral surfaces of the first and second arms 105, 110. The bosses 145, 150 project outwardly beyond the outer surfaces of the arms 105, 110. The applicator engages the clip 100 using the bosses 145, 150.

Clips according to principles of the invention may be comprised, in whole or in part of metals such as stainless steel, titanium, tantalum, or alloys thereof. Bioabsorbable and radiolucent versions may be comprised of a one-piece integral polymeric body formed from a suitable strong biocompatible engineering plastic such as the type commonly used for surgical implants. Examples include biocompatible polydioxanone polymer, acetal polyoxymethylene (POM), polyethylene terephthalate (PET), polybutylene terephthalate (PBT), polyoxymethylene, or other thermoplastic materials having similar properties that can be injection-molded, extruded or otherwise processed into like articles.

Figures 10, 11:
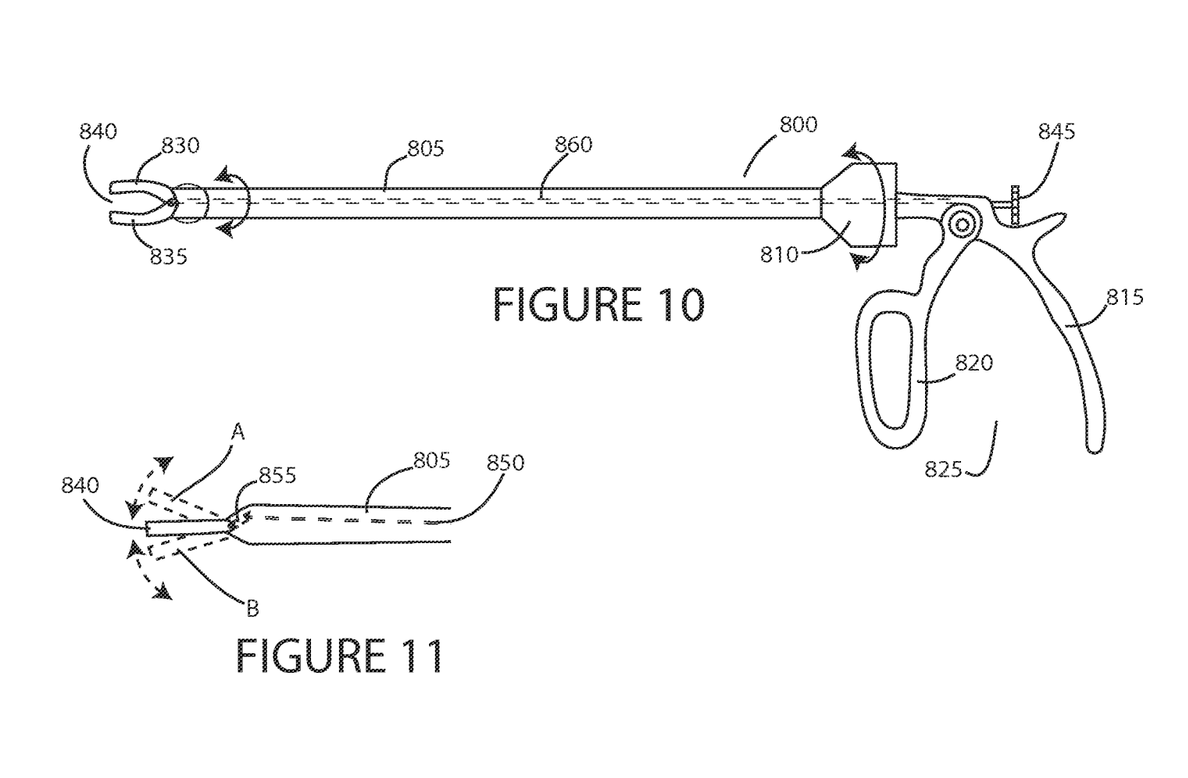
FIG. 10 is a side view of an exemplary applicator for a surgical clip according to principles of the invention.
FIG. 11 is a side view of an exemplary pivoting tip of an applicator for a surgical clip according to principles of the invention.

In use, the clip 100 is positioned and compressed into a locked position using an applicator 800, as shown in FIG. 10. The applicator 800 includes a forceps-type applier having a conformal jaw assembly 840 used to grip and maintain alignment of the clip during placement and compressive deformation. The proximal end of the applicator 800 includes a handle assembly 825 with a stationary element 815 and a movable (e.g., pivoting) element 820. A linkage 860, not shown, contained within an elongated tubular shaft 805, operably couples the movable handle element 820 to the conformal jaw assembly 840. The shaft 805 preferably fits through a 10 mm trocar. The distal end of applicator 800 generally comprises the conformal jaw assembly 840 having opposing pivotable jaws 830, 835 which have respective jaw recesses adapted to engage and retain bosses 145, 150 of the clip 100. Closure of the jaws 830, 835 of the applicator 800 compresses the held clip 100. This causes the first and second arms 105, 110 of the clip 100 to close around a vessel, organ or tissue with clamping sides of the first and second arms 105, 110 contacting the outer surface of the engaged vessel, organ or tissue. As the clip is compressed, any portion of the engaged vessel, organ or tissue or surrounding tissue in the path of the male pin will be penetrated. As compression continues, the male pin begins to contact the female aperture. Further pivotal movement by the applicator urges the pin into the aperture until the head of the pin is forced through the aperture. Thereafter, the shank of the male pin is matingly seated in the female aperture. This is the locked position. Upon release of the applicator instrument, the clip remains in the locked position.

Uniquely, the exemplary clip applicator includes an angularly adjustable jaw assembly 840, as conceptually illustrated in FIG. 11. Rotation of the cuff 810 of the applicator is translated into and causes pivotal motion of the jaw assembly 840. Rotating the cuff in one direction causes pivoting motion in one direction A. Rotating the cuff in the other direction causes pivoting motion in the opposite direction B.

Various linkages may be used to translate rotational motion of the cuff into pivoting motion of the jaw assembly 840. By way of example and not limitation, rotation of the cuff may rotate a threaded rod 850 operably coupled to a cam or lever 855 connected to the pivoting jaw assembly 840. In another embodiment, a separate control, such as a thumbscrew 845, is provided to adjust the linkage that causes the jaw assembly to pivot.

Figure 12:
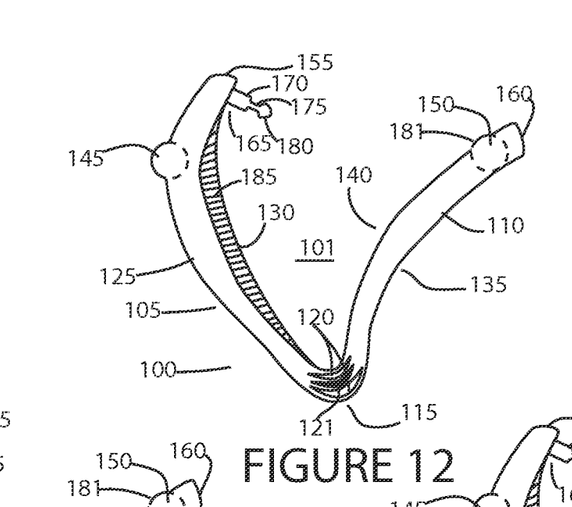
FIG. 12 is a plan view of an exemplary surgical clip according to principles of the invention.
Figure 13:
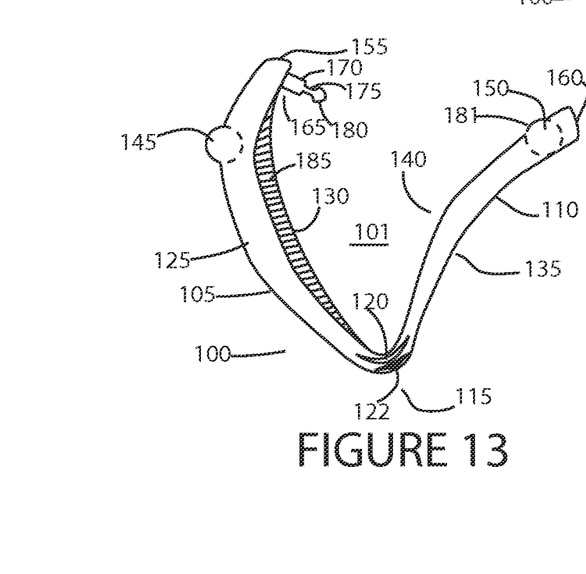
FIG. 13 is a plan view of an exemplary surgical clip according to principles of the invention.
Figure 14:
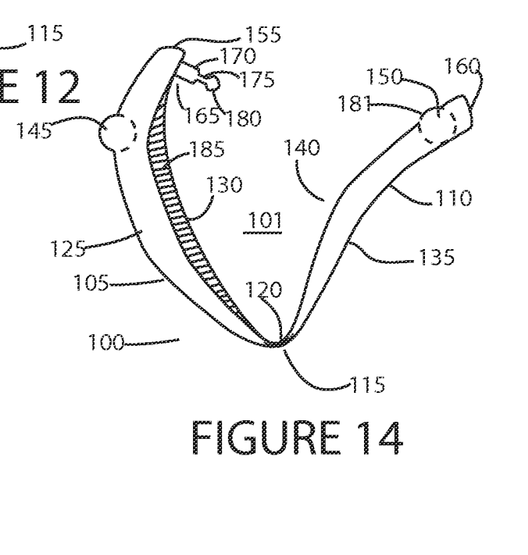
FIG. 14 is a plan view of an exemplary surgical clip according to principles of the invention.

With reference to FIGS. 12 through 14, various exemplary embodiments of a clip 100 according to principles of the invention are illustrated. The hinged sections of the clips vary. In each case, the width and/or thickness of the hinge section 115 is less than the average thickness of a clamping arm. In each case the hinged section 115 includes one or more apertures 120 to facilitate bending. In FIGS. 12 and 13, the hinged section includes a boss 122 to facilitate manipulation. The boss 122 (i.e., a hinge boss) is a protruding feature that can be gripped by the applicator during insertion. The shape and position of the hinge boss may vary within the scope of the invention.

Thus, the clip may include a unique arrangement of bosses. As discussed above, there may be bosses at the free end of the arms. There may also be one or more bosses, such as boss 122, at or near the hinge. The applicator will hold the clip by its bosses until the clip is released from the applicator. Gripping the boss at the hinge until the clip is released provides enhanced control of the clip. Specifically, gripping the boss at the hinge may prevent unwanted angulation of the clip.

Figure 15:
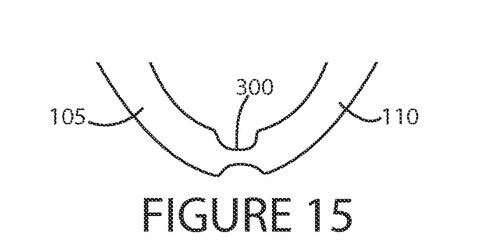
FIG. 15 is a plan view of a hinged portion of an exemplary surgical clip according to principles of the invention.
Figure 16:
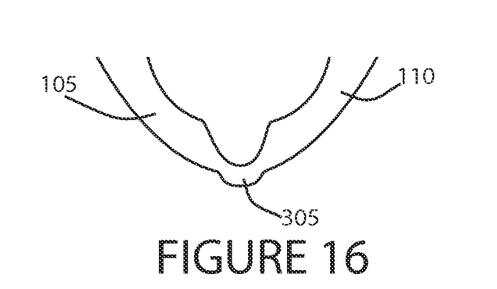
FIG. 16 is a plan view of a hinged portion of an exemplary surgical clip according to principles of the invention.
Figure 17:
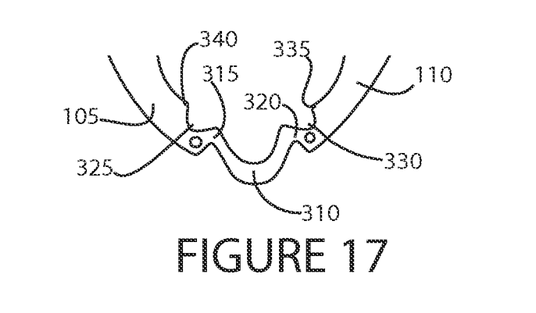
FIG. 17 is a plan view of a hinged portion of an exemplary surgical clip according to principles of the invention.

Referring now to FIGS. 15 through 16, various exemplary alternative hinge configurations are illustrated. The embodiment in FIG. 15 shows a tapered hinge 300. The embodiment in FIG. 16 is a tapered and outwardly curved hinge 305 (i.e., curved away from the clamping space between the clamping arms. In FIG. 17, the hinge 310 is outwardly curved. The hinge also features shoulder sections 315, 320 which define the point of transition from clamping arms 105, 110 to the hinge 310. The shoulder sections include a recess 325, 330 in each arm followed by an angled protrusion 315, 320. In each case, the curvature of the hinge departs from the curvature of the arms. In each case, the hinge is configured to maintain a space between the hinge surface and the engaged vessel or tissue. In each case, the hinge has a reduced width or thickness, relative to the thickness or average thickness of the clamping arms. In each case the hinge can be cut without damaging a clamped vessel or tissue.

Figure 18:
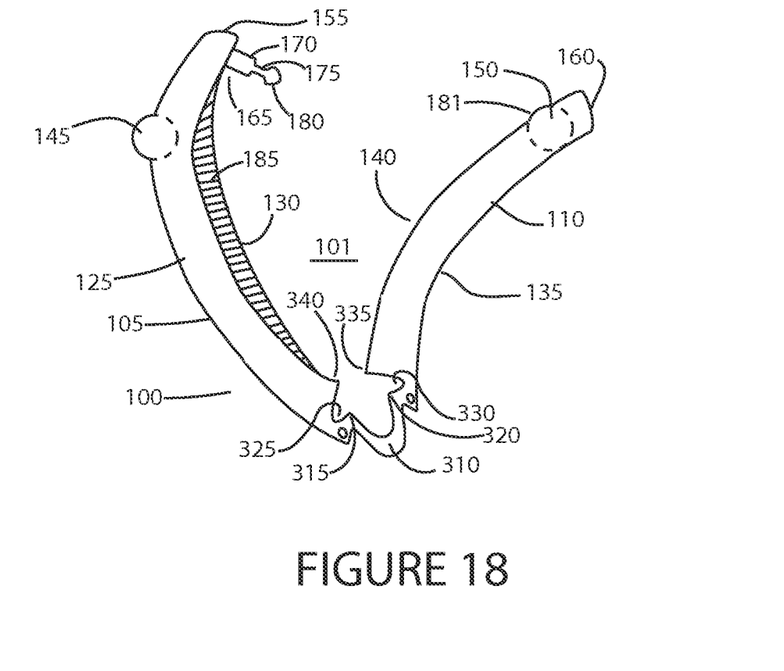
FIG. 18 is a plan view of an exemplary surgical clip according to principles of the invention.

Referring now to FIG. 18, an exemplary embodiment of a clip 100 with a hinge according to FIG. 17 is shown. The hinge 310 is outwardly curved. The hinge includes shoulder sections defining points of transition from clamping arms 105, 110 to the outwardly curved hinge 310. The shoulder sections include a recess 325, 330 in each arm followed by an angled protrusion 315, 320. The thickness and or width of the hinge is less than about half of the average thickness and/or width of the arms. Thus, the curvature of the hinge 310 departs from the curvature of the arms. The hinge 310 is configured to maintain a space between the hinge surface and the engaged vessel or tissue. The hinge 310 has a reduced width or thickness, relative to the thickness or average thickness of the clamping arms. When the clip 100 is closed around a vessel, the interior ends 335, 340 (i.e., hinged ends or ends leading to the hinge) of the clamping arms 105, 110, are adjacent or abutting one another. A clamped vessel and/or tissue does not substantially extend into the space between the interior ends 335, 340 of the clamping arms 105, 110 and the hinge 310. Thus, the hinge 310 may be cut without also cutting the clamped tissue or vessel.

A clip according to principles of the invention can be sized to accommodate various vessels. In an exemplary embodiment, the clips are sized to work with laparoscopic procedures, meaning that it preferably can fit through a 10 mm trocar. It may pass through the trocar in a partially clamped state. After passing through the trocar, if the clip was partially compressed, then the jaws of the applicator and the clip will expand into a fully opened state. Thus, other than being sized for use with a laparoscopic procedure, the size of the clip may vary considerably to accommodate various vessels.

Figure 19:
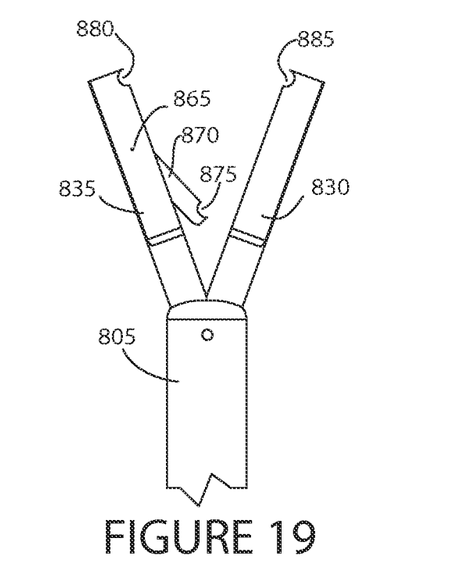
FIG. 19 is a plan view of hinged jaws of an exemplary surgical clip applicator according to principles of the invention.
Figure 20:
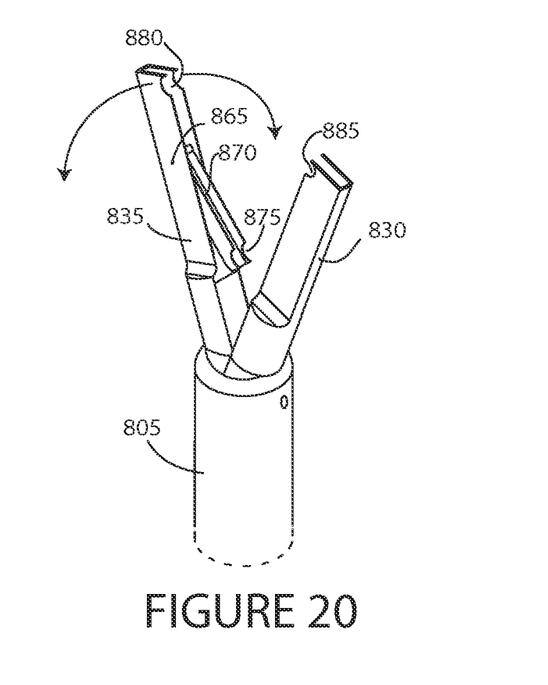
FIG. 20 is a perspective view of hinged jaws of an exemplary surgical clip applicator according to principles of the invention.

Referring now to FIGS. 19 and 20, views of a hinged jaw assembly of an exemplary surgical clip applicator according to principles of the invention are provided. In addition to opposed hinged jaws 830, 835, the assembly includes a holder for a hinge boss. The free ends of the holder include cutouts 880, 885 for engaging bosses near the free ends of the arms of an engaged clip. In the embodiment shown in the Figures, the holder comprises a pivoting arm 870 with a cutout 875 for engaging a boss on the hinged section of an engaged clip. The pivoting arm is biased (e.g., spring biased) to an open position as shown in FIGS. 19 and 20. A pivot pin 865 couples the hinged holder to an arm 835 of the jaw assembly. As the jaws 830, 835 are closed, the pivoting arm pivots to a closed position. In the exemplary embodiment, the jaw arms 830, 835 and pivoting arm 870 have a U-shaped cross section shape. The U of at least one jaw is wide enough to receive the pivoting arm 870 in a nested fashion as the jaws are closed and the pivoting arm 870 is pivoted to closed position.

Figure 21:
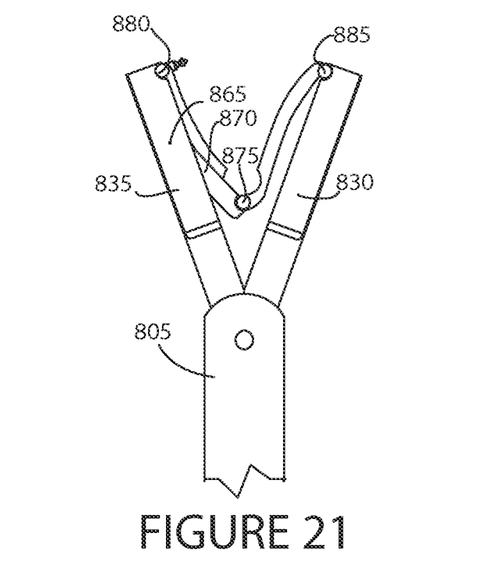
FIG. 21 is a plan view of hinged jaws of an exemplary surgical clip applicator with a clip having bosses at the free end and a boss at the hinge for gripping according to principles of the invention.
Figure 22:
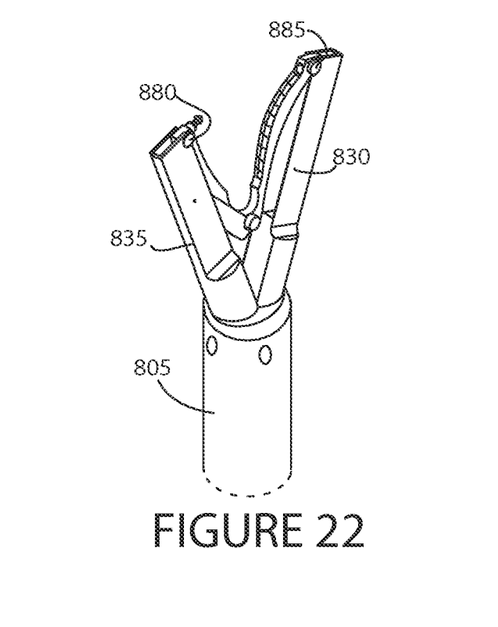
FIG. 22 is a perspective view of hinged jaws of an exemplary surgical clip applicator with a clip having bosses at the free end and a boss at the hinge for gripping according to principles of the invention.

In FIGS. 21 and 22, an exemplary clip according to principles of the invention is shown engaged by the jaws. The boss near the hinge is engaged by the holder comprising the pivoting arm 870. Gripping the boss at the hinge prevents unwanted angulation of the clip during manipulation and use.

Figure 23:
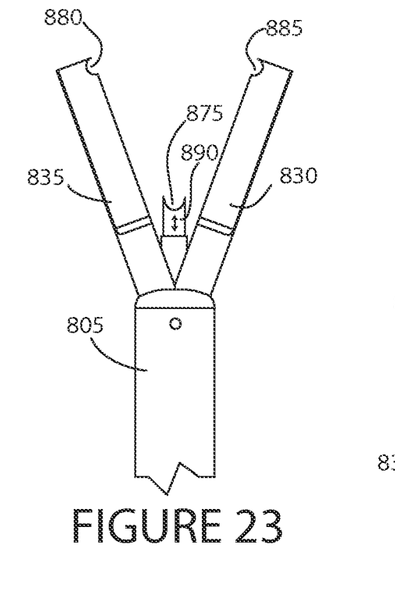
FIG. 23 is a plan view of hinged jaws of an exemplary surgical clip applicator with a holder for engaging a boss at a hinge of a clip according to principles of the invention.
Figure 24:
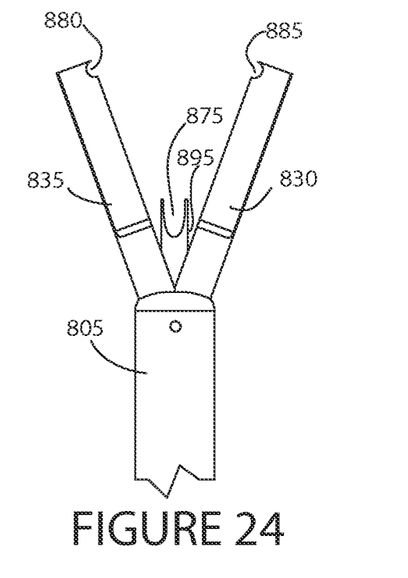
FIG. 24 is a plan view of hinged jaws of an exemplary surgical clip applicator with a holder for engaging a boss at a hinge of a clip according to principles of the invention.
Figure 25:
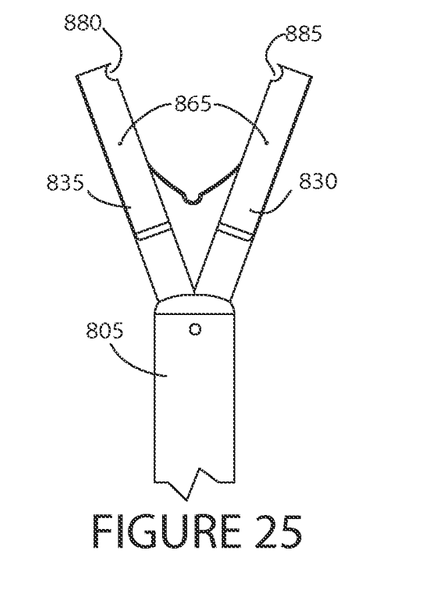
FIG. 25 is a perspective view of hinged jaws of an exemplary surgical clip applicator with a holder for engaging a boss at a hinge of a clip according to principles of the invention.

Referring now to FIGS. 23 to 25, views of alternative exemplary hinged jaw assemblies according to principles of the invention are provided. The embodiment in FIG. 23 includes a hinge boss holder comprising a biased (e.g., spring biased) telescopic arm 890 with a cutout 875 at its free end to engage a boss at the hinge of a clip. The embodiment in FIG. 24 includes a hinge boss holder comprising a stationary arm 895 with an elongated cutout 877 at its free end to constrain a boss at the hinge of a clip, and yet allow linear movement of the boss during compression. The embodiment in FIG. 25 includes a hinge boss holder comprising a leaf spring 896 on the outer top side of the jaws, with a midsection bight (i.e., curved segment) 897 to engage a boss at the hinge of a clip. Each of these embodiments illustrate exemplary holders configured to grip the boss at the hinge, thereby preventing unwanted angulation of the clip during manipulation and use.

While an exemplary embodiment of the invention has been described, it should be apparent that modifications and variations thereto are possible, all of which fall within the true spirit and scope of the invention. With respect to the above description then, it is to be realized that the optimum relationships for the components and steps of the invention, including variations in order, form, content, function and manner of operation, are deemed readily apparent and obvious to one skilled in the art, and all equivalent relationships to those illustrated in the drawings and described in the specification are intended to be encompassed by the present invention. The above description and drawings are illustrative of modifications that can be made without departing from the present invention, the scope of which is to be limited only by the following claims. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents are intended to fall within the scope of the invention as claimed.

What is claimed is:

1. A surgical clip comprising:
a pair of opposed arms joined at a hinged end by an integrally formed flexible hinge, the pair of opposed arms comprising:
a first arm having a first arm width, the first arm comprising a clamping side with a plurality of spaced-apart longitudinally-oriented wedge shaped protrusions, each of the wedge shaped protrusions comprising chamfered surfaces extending from outer lateral sides of the first arm and converging at a vertex such that each of the wedge shaped protrusions extends across the first arm width; and
a second arm having a second arm width, the second arm comprising a clamping side with a plurality of spaced-apart longitudinally-oriented V-shaped trough segments and comprising chamfered surfaces that converge at a vertex, the V-shaped trough segments extending across the second arm width, such that the clamping side of the second arm faces the clamping side of the first arm, and the V-shaped trough segments conform to the shape of the wedge shaped protrusions and are aligned to receive the wedge shaped protrusions,
each arm having a free end, one of the first and second arms including a male locking pin near the free end, and the other of the first and second arms including a female aperture near the free end, the first and second arms movable from an open configuration in which the male locking pin is spaced from the female aperture to a locked configuration in which the male locking pin is engaged with the female aperture, said male locking pin including a tissue piercing head, said tissue piercing head being configured to penetrate tissue in the path of the male locking pin when the male locking pin is urged towards the female aperture, and said female aperture being configured to engage the tissue piercing head of the male locking pin and resist withdrawal of the head when the head has been urged through the female aperture into the locked configuration.

2. The surgical clip of claim 1 wherein the flexible hinge is a U-shaped segment that extends from the hinged end of each arm of the pair of opposed arms.

3. The surgical clip of claim 2 further including a shoulder between the flexible hinge and the hinged end of each arm of the pair of opposed arms, each shoulder comprising a recess at the end of each arm followed by angled protrusion towards a space between the pair of opposed arms.

4. The surgical clip of claim 3, wherein the hinged arms of the pair of opposed arms are configured to abut each other when the surgical clip is closed.

5. The surgical clip of claim 4, wherein a clamped object does not contact the flexible hinge when the surgical clip is closed.

6. The surgical clip of claim 3, wherein a clamped object does not contact the flexible hinge when the surgical clip is closed and the hinge may be cut to release the clamp.

7. The surgical clip of claim 3, wherein a clamped object does not contact the flexible hinge when the surgical clip is closed and the hinge may be cut, without contacting the clamped object, to release the clamp.

8. The surgical clip of claim 3, wherein an empty space is maintained between the hinged arms of the pair of opposed arms and the flexible hinge.

9. The surgical clip of claim 2 wherein the flexible hinge has a hinge thickness and width, and each arm of the pair of opposed arms has an average thickness and width, and the width of the flexible hinge is less than the average width of each arm of the pair of opposed arms.

10. The surgical clip of claim 2 wherein the flexible hinge has a hinge thickness and width, and each arm of the pair of opposed arms has an average thickness and width, and the thickness of the flexible hinge is less than the average thickness of each arm of the pair of opposed arms.

11. The surgical clip of claim 2 wherein the clip is comprised of a bioabsorbable plastic.

12. The surgical clip of claim 1 wherein the clamping sides of the first and second arms further comprise non-slip protrusions.

13. The surgical clip of claim 1 wherein the clamping sides of the first and second arms further comprise non-slip protruding ribs.

14. The surgical clip of claim 1, further comprising:
a pair of cylindrical bosses formed coaxially on opposed lateral surfaces of the pair of opposed arms, said pair of cylindrical bosses projecting outwardly from the pair of opposed arms, and
at least one boss on the hinged end, said at least one boss projecting outwardly from the hinged end.

15. The surgical clip of claim 1, wherein the female aperture is defined in the first or second arm in axially spaced relation from the free end, and extends from the clamping side to an outer side of the first or second arm.

16. The surgical clip of claim 1, wherein the female aperture includes a tapered section configured to resist withdrawal of the male locking pin when the first and second arms are in the locked configuration.

17. The surgical clip of claim 1, wherein the chamfered surfaces of the V-shaped trough segments of the second arm extend from outer lateral sides of the second arm to the vertex.

* * * * *